US009163086B2

(12) United States Patent
Qin et al.

(10) Patent No.: US 9,163,086 B2
(45) Date of Patent: Oct. 20, 2015

(54) METHODS AND COMPOSITIONS FOR THE TREATMENT OF PROLIFERATIVE AND PATHOGENIC DISEASES

(75) Inventors: Xuebin Qin, Westwood, MA (US); Weiguo Hu, Quincy, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 475 days.

(21) Appl. No.: 13/391,124

(22) PCT Filed: Aug. 18, 2010

(86) PCT No.: PCT/US2010/045874
§ 371 (c)(1),
(2), (4) Date: Jul. 9, 2012

(87) PCT Pub. No.: WO2011/022472
PCT Pub. Date: Feb. 24, 2011

(65) Prior Publication Data
US 2012/0269801 A1    Oct. 25, 2012

Related U.S. Application Data

(60) Provisional application No. 61/234,918, filed on Aug. 18, 2009.

(51) Int. Cl.
*C07K 16/00*    (2006.01)
*C12P 21/08*    (2006.01)
*A61K 39/395*   (2006.01)
*C07K 16/28*    (2006.01)
*A61K 39/00*    (2006.01)

(52) U.S. Cl.
CPC .......... *C07K 16/2896* (2013.01); *C07K 16/005* (2013.01); *A61K 2039/505* (2013.01); *C07K 16/28* (2013.01); *C07K 2317/21* (2013.01); *C07K 2317/515* (2013.01); *C07K 2317/55* (2013.01); *C07K 2317/73* (2013.01)

(58) Field of Classification Search
None
See application file for complete search history.

(56) References Cited

U.S. PATENT DOCUMENTS

| 4,816,567 | A | 3/1989 | Cabilly et al. |
| 5,821,337 | A | 10/1998 | Carter et al. |
| 6,054,297 | A | 4/2000 | Carter et al. |
| 6,680,209 | B1 | 1/2004 | Buechler et al. |
| 2002/0122807 | A1 | 9/2002 | Dan et al. |
| 2003/0039649 | A1 | 2/2003 | Foote |
| 2003/0166565 | A1 | 9/2003 | Sims |
| 2005/0208043 | A1 | 9/2005 | Adams et al. |
| 2005/0276802 | A1 | 12/2005 | Adams et al. |
| 2006/0140963 | A1* | 6/2006 | Young et al. ............... 424/155.1 |

FOREIGN PATENT DOCUMENTS

| CN | 1920565 A | 2/2007 |
| CN | 101389658 A | 3/2009 |
| EP | 0332424 A2 | 9/1989 |
| EP | 0338745 A1 | 10/1989 |
| EP | 0239400 B1 | 8/1994 |
| WO | WO-8909622 A1 | 10/1989 |
| WO | WO-9321319 A1 | 10/1993 |
| WO | WO-2005076696 A2 | 8/2005 |
| WO | WO-2005108419 A1 | 11/2005 |
| WO | WO-2008085366 A2 | 7/2008 |
| WO | WO-2008121402 A1 | 10/2008 |
| WO | WO-2009014560 A1 | 1/2009 |
| WO | WO-2010078329 A1 | 7/2010 |

OTHER PUBLICATIONS

Lallinger et al. "Efficacy of Immune Therapy in Early Experimental Naegleria fowleri Meningitis" Infection & Immunity, 1987, pp. 1289-1293.*
Amet et al. "CD59 incorporation protects hepatitis C virus against complement-mediated destruction" Hepatology, 55(2), 354-363, 2012.*
Hu et al. "A high-affinity inhibitor of human CD59 enhances complement-mediated virolysis of HIV-1: implications for treatment of HIV-1/AIDS" J Immunol. 2010, 184(1), pp. 359-368.*
Altschul et al. "Basic Local Alignment Search Tool." *J. Mol. Biol.* 215.3(1990):403-410.
Bernet et al. "Viral Mimicry of the Complement System." *J. Biosci.* 28.3(2003):249-264.
Boerner et al. "Production of Antigen-Specific Human Monoclonal Antibodies from in vitro-Primed Human Splenocytes." *J. Immunol.* 147.1(1991):86-95.
Boulianne et al. "Production of Functional Chimaeric Mouse/Human Antibody." *Nature.* 312.5995(1984):643-646.
Bowie et al. "Deciphering the Message in Protein Sequences: Tolerance to Amino Acid Substitutions." *Science.* 247.4948(1990):1306-1310.
Brodeur et al. "Mouse-Human Myeloma Partners for the Production of Heterohybridomas." *Monoclonal Antibody Production Techniques and Applications.* Schook, ed. New York: Marcel Dekker, Inc. (1987):51-63.
Carrillo et al. "The Multiple Sequence Alignment Problem in Biology." *SIAM J. Appl. Math.* 48.5(1988):1073-1082.
Carter. "Improving the Efficacy of Antibody-Based Cancer Therapies." *Nat. Rev. Cancer.* 1.2(2001):118-129.
Chaudhary et al. "A Rapid Method of Cloning Functional Variable-Region Antibody Genes in *Escherichia coli* as Single-Chain Immunotoxins." *PNAS.* 87.3(1990):1066-1070.

(Continued)

*Primary Examiner* — Daniel E Kolker
*Assistant Examiner* — James Rogers
(74) *Attorney, Agent, or Firm* — Mintz, Levin, Cohn, Ferris, Glovsky and Popeo, P.C.

(57) ABSTRACT

The invention features proteins including an antibody, or functional derivatives thereof, that bind hCD59 and have the activity of domain 4 of the *Streptococcus* intermedins intermedilysin (ILY) protein. In order to prevent the independent induction of CDC and ADCC, the antibodies of the invention can bind the same hCD59 epitope as ILYd4 and/or contain modifications that disrupt the interaction between the antibody and complement.

34 Claims, No Drawings

(56) References Cited

OTHER PUBLICATIONS

Chorev et al. "A Dozen Years of Retro-Inverso Peptidomimetics." *Acc. Chem. Res.* 26.5(1993):266-273.
Cole et al. "The EBV-Hybridoma Technique and its Application to Human Lung Cancer." *Monoclonal Antibodies and Cancer Therapy*. Reisfeld et al., eds. New York: Alan R. Liss, Inc. (1985):77-96.
Devereux et al."A Comprehensive Set of Sequence Analysis Programs for the VAX." *Nucl. Acids Res.* 12.1(1984):387-395.
Fritzinger et al. "Identification of a *Naegleria fowleri* Membrane Protein Reactive with Anti-Human CD59 Antibody." *Infect. Immun.* 74.2(2006):1189-1195.
Ge et al. "rILYd4, a Human CD59 Inhibitor, Enhances Complement-Dependent Cytotoxicity of Ofatumumab Against Rituximab-Resistant B-Cell Lymphoma Cells and Chronic Lymphocytic Leukemia." *Clin. Cancer. Res.* 17.21(2011):6702-6711.
GenBank Accession No. AB029317, Jan. 21, 2000.
GenBank Accession No. BAE16324, Jul. 26, 2005.
Giddings et al. "Human CD59 is a Receptor for the Cholesterol-Dependent Cytolysin Intermedilysin." *Nat. Struct. Mol. Biol.* 11.12(2004):1173-1178.
Hu et al. "A High-Affinity Inhibitor of Human CD59 Enhances Complement-Mediated Virolysis of HIV-1: Implications for Treatment of HIV-1/AIDS." *J. Immunol.* 184.1(2010):359-368.
Hu et al. "Domain 4 of ILY Sensitizes Antibody Therapy on Cancer and HIV Through Abrogating Human CD59 Function." *FASEB J.* 22(2008):522. (Abstract #lb522).
Hu et al. "Rapid Conditional Targeted Ablation of Cells Expressing Human CD59 in Transgenic Mice by Intermedilysin." *Nat. Med.* 14.1(2008):98-103.
Hughes et al. Characterisation of the High Affinity Interaction Between the Human.
Complement Regulator CD59 and the *Staphylococcus Intermedius* Toxin, Intermedilysin. *Mol. Immunol.* 44(2007):3985. (Abstract #P119).
Iannello et al. "Role of Antibody-Dependent Cell-Mediated Cytotoxicity in the Efficacy of Therapeutic Anti-Cancer Monoclonal Antibodies." *Cancer Metastat. Rev.* 24(2005):487-499.
Jones et al. "Replacing the Complementarity-Determining Regions in a Human Antibody with Those from a Mouse." *Nature.* 321.6069(1986):522-525.
Juhl et al. "Frequent Expression of Complement Resistance Factors CD46, CD55, and CD59 on Gastrointestinal Cancer Cells Limits the Therapeutic Potential of Monoclonal Antibody 17-1A." *J. Surg. Oncol.* 64.3(1997):222-230.
Kozbor et al. "A Human Hybrid Myeloma for Production of Human Monoclonal Antibodies." *J. Immunol.* 133.6(1984):3001-3005.
Marks et al. "By-Passing Immunization." *J. Mol. Biol.* 222.3(1991):581-597.
Matsushita et al. "Ex vivo Neutralization of HIV-1 Quasi-Species by a Broadly Reactive Humanized Monoclonal Antibody KD-247." *Hum. Antibodies.* 14.3-4(2005):81-88.
Morrison et al. "Chimeric Human Antibody Molecules: Mouse Antigen-Binding Domains with Human Constant Region Domains." *PNAS.* 81.21(1984):6851-6855.
Nagamune et al. "A Cell Membrane Modification Technique Using Domain 4 of Intermedilysin for Immunotherapy Against Cancer." *Anticancer Res.* 24(2004):3367-3372.
Nagamune et al. "The Human-Specific Action of Intermedilysin, A Homolog of Streptolysin O, is Dictated by Domain 4 of the Protein." *Microbiol. Immunol.* 48(2004):677-692.
Nakamura et al. "Virolysis and in Vitro Neutralization of HIV-1 by Humanized Monoclonal Antibody hNM-01." *Hybridoma.* 19.6(2000):427-434.
Neuberger et al. "A Hapten-Specific Chimaeric IgE Antibody With Human Physiological Effector Function." *Nature.* 314.6008(1985):268-270.
Neuberger et al. "Recombinant Antibodies Possessing Novel Effector Functions." *Nature.* 312.5995(1984):604-608.
Nguyen et al. "Evidence for Budding of Human Immunodeficiency Virus Type 1 Selectively from Glycolipid-Enriched Membrane Lipid Rafts." *J. Virol.* 74.7(2000):3264-3272.
Ohkura et al. "Structural Analysis of Human Specifid Cytolysin Intermedilysin Aiming Application to Cancer Immunotherapy." *Anticancer Res.* 24(2004):3343-3353.
Parizade et al. "Functional and Antigenic Similarities Between a 94-kD Protein of Schistosoma mansoni (SCIP-1) and Human CD59." *J. Exp. Med.* 179.5(1994):1625-1636.
Phelan et al. "A General Method for Constraining Short Pepties to an α-Helical Conformation." *J. Am. Chem. Soc.* 119.3(1997):455-460.
Polekhina et al. "Insights into the Action of the Superfamily of Cholesterol-Dependent Cytolysins from Studies of Intermedilysin." *PNAS.* 102.3(2005):600-605.
Presta. "Antibody Engineering for Therapeutics." *Curr. Opin. Struct. Biol.* 2(1992):593-596.
Rautemaa et al. "Herpes Simplex Virus 1 Infected Neuronal and Skin Cells Differ in their Susceptibility to Complement Attack." *Immunol.* 106.3(2002):404-411.
Riechmann et al. "Reshaping Human Antibodies for Therapy." *Nature.* 332.6162(1988):323-327.
Saifuddin et al. "Role of Virion-Associated Glycosylphosphatidylinositol-Linked Proteins CD55 and CD59 in Complement Resistance of Cell Line-Derived and Primary Isolates of HIV-1." *J. Exp. Med.* 182.2(1995):501-509.
Shimada et al. "The C-Terminal Domain of Perfringolysin O is an Essential Cholesterol-Binding Unit Targeting to Cholesterol-Rich Microdomains." *Eur. J. Biochem.* 269(2002):6195-6203.
Smith et al. "Antibody Phage Display Technologies With Special Reference to Angiogenesis." *FASEB J.* 19.3(2005):331-341.
Soltani et al. "Specific Protein-Membrane Contacts are Required for Prepore and Pore Assembly by a Cholesterol-Dependent Cytolysin." *J. Biol. Chem.* 282(2007):15709-15716.
Spiller et al. "Neutralization of Cytomegalovirus Virions: The Role of Complement." *J. Infect. Dis.* 176.2(1997):339-347.
Stoiber et al. "Complement-Opsonized HIV: The Free Rider on its Way to Infection." *Mol. Immunol.* 42.2(2005):153-160.
Takeda et al. "Construction of Chimaeric Processed Immunoglobulin Genes Containing Mouse Variable and Human Constant Region Sequences." *Nature.* 314.6010(1985):452-454.
Takei et al. "Analysis of Changes in CD20, CD55, and CD59 Expression on Established Rituximab-Resistant B-Lymphoma Cell Lines." *Leuk. Res.* 30.5(2006):625-631.
Vaswani et al. "Humanized Antibodies as Potential Therapeutic Drugs." *Ann. Allergy Asthma Immunol.* 81.2(1998):105-115.
Verhoeyen et al. "Reshaping Human Antibodies: Grafting an Antilysozyme Activity." *Science.* 239.4847(1988):1534-1536.
Weis et al. "Streptolysin O: The C Terminal, Tryptophan-Rich Domain Carries Functional Sites for Both Membrane Binding and Self-Interaction but not for Stable Oligomerization." *Biochim. Biophys. Acta.* 1510(2001):292-299.
Winter et al. "Making Antibodies by Phage Display Technology." *Annu. Rev. Immunol.* 12(1994):433-455.
You et al. "Application of a Novel Inhibitor of Human CD59 for the Enhancement of Complement-Dependent Cytolysis on Cancer Cells." *Cell. Mol.lmmunol.* 8.2(2011):157-163.
Tilley et al. "Structural Basis of Pore Formation by the Bacterial Toxin Pneumolysin." *Cell.* 121.2(2005):247-256.

* cited by examiner

SEQUENCE LISTING

<160> NUMBER OF SEQ ID NOS: 22

<210> SEQ ID NO 1
<211> LENGTH: 114
<212> TYPE: PRT
<213> ORGANISM: Artificial Sequence
<220> FEATURE:
<223> OTHER INFORMATION: Synthetic Construct

<400> SEQUENCE: 1

Gly Ala Leu Thr Leu Asn His Asp Gly Ala Phe Val Ala Arg Phe Tyr
1               5                   10                  15

Val Tyr Trp Glu Glu Leu Gly His Asp Ala Asp Gly Tyr Glu Thr Ile
            20                  25                  30

Arg Ser Arg Ser Trp Ser Gly Asn Gly Tyr Asn Arg Gly Ala His Tyr
        35                  40                  45

Ser Thr Thr Leu Arg Phe Lys Gly Asn Val Arg Asn Ile Arg Val Lys
    50                  55                  60

Val Leu Gly Ala Thr Gly Leu Ala Trp Glu Pro Trp Arg Leu Ile Tyr
65                  70                  75                  80

Ser Lys Asn Asp Leu Pro Leu Val Pro Gln Arg Asn Ile Ser Thr Trp
                85                  90                  95

Gly Thr Thr Leu His Pro Gln Phe Glu Asp Lys Val Val Lys Asp Asn
            100                 105                 110

Thr Asp

<210> SEQ ID NO 2
<211> LENGTH: 56
<212> TYPE: PRT
<213> ORGANISM: Artificial Sequence
<220> FEATURE:
<223> OTHER INFORMATION: Synthetic Construct

<400> SEQUENCE: 2

Arg Asn Ile Arg Val Lys Val Leu Gly Ala Thr Gly Leu Ala Trp Glu
1               5                   10                  15

Pro Trp Arg Leu Ile Tyr Ser Lys Asn Asp Leu Pro Leu Val Pro Gln
            20                  25                  30

Arg Asn Ile Ser Thr Trp Gly Thr Thr Leu His Pro Gln Phe Glu Asp
        35                  40                  45

Lys Val Val Lys Asp Asn Thr Asp
    50                  55

<210> SEQ ID NO 3
<211> LENGTH: 638
<212> TYPE: DNA
<213> ORGANISM: Artificial Sequence
<220> FEATURE:
<223> OTHER INFORMATION: Synthetic Construct

<400> SEQUENCE: 3
gagctcgtgt tgacgcagtc tccagccacc ctgtctttgt ctccagggga aagagccacc     60
ctctcctgcg ggccagtca gagtgtcagc agcagctact tagcctggta ccagcagaaa    120
cctggccgct cccaggctcc tcatctatgg tgcatccagc agggccactg gcatcccaga    180
caggttcagt ggcagtgggt ctgggacaga cttcactctc accatcagca gactggagcc    240
tgaagatttt gcattattac tgtcagcagt atggtagctc acctccagtc accttcggcc    300
aagggacacg actggagatt aaacgaactg tggctgcacc atctgtcttc atcttcccgc    360

```
catctgatga gcagttgaat cggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaggaag cacctacagc ctcagcagca ccctgacgct      540
gagcaaagca gactacgaga aacacaaagt ctacgcctgc gaagtcaccc atcagggcct      600
gagcttgccc gtcacaaaga gcttcaacag ggagatgt                              638
```

```
<210> SEQ ID NO 4
<211> LENGTH: 215
<212> TYPE: PRT
<213> ORGANISM: Artificial Sequence
<220> FEATURE:
<223> OTHER INFORMATION: Synthetic Construct

<400> SEQUENCE: 4
```

Glu Leu Val Leu Thr Gln Ser Pro Ala Thr Leu Ser Leu Ser Pro Gly
1               5                  10                  15

Glu Arg Ala Thr Leu Ser Cys Gly Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Val Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Leu Pro Val Thr Lys
        195                 200                 205

Ser Phe Asn Arg Gly Glu Cys
    210                 215

```
<210> SEQ ID NO 5
<211> LENGTH: 665
<212> TYPE: DNA
<213> ORGANISM: Artificial Sequence
<220> FEATURE:
<223> OTHER INFORMATION: Synthetic Construct

<400> SEQUENCE: 5
aaggtgcagc tggtggagtc tggggctgag gtgaagaagc ctggggcctc agtgaaggtc       60
tcctgcaagg cttctggata caccttcacc agttatgata tcaactgggt gcgacaggcc      120
actggacggg cttgagtgga tgggatggat gaaccctaac agtggtaaca caggctatgc      180
acagaagttc cagggcagag tcaccatgac caggaacacc tccataagca cagcctacat      240
```

```
ggagctgagc agctagatct gaggacacgg ccgtgtatta ctgtgcgaga ggcaaaggga      300
gtggttatta taactactgg ggccagggca ccctggtcac cgtctcctct gcctccacca      360
agggcccatc ggtcttcccc tgcacccgcc tccaagagca cctctggggg cacagcggcc      420
ctgggctgcc tggtcaagga ctacttcccc gaaccggtga cggtgtcgtg gaactcaggc      480
gccctgacca gcggcgtgca cacctcccgc tgtcctacag tcctcaggac tctactccct      540
cagcagcgtg gtgaccgtgc cctccagcag cttgggcacc cagacctaca tctgcaacgt      600
gaatcacaag cccagcaaca ccaaggtgga cagaagttga gcccaaatct tgtgacaaaa      660
ctagt                                                                  665
```

<210> SEQ ID NO 6
<211> LENGTH: 224
<212> TYPE: PRT
<213> ORGANISM: Artificial Sequence
<220> FEATURE:
<223> OTHER INFORMATION: Synthetic Construct

<400> SEQUENCE: 6

```
Lys Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Gly Ser Gly Tyr Tyr Asn Tyr Trp Gly Gln Gly Thr
            100                 105                 110

Leu Val Thr Val Ser Ser Ala Ser Thr Lys Gly Pro Ser Val Phe Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr Ser
    210                 215                 220
```

<210> SEQ ID NO 7
<211> LENGTH: 637
<212> TYPE: DNA
<213> ORGANISM: Artificial Sequence
<220> FEATURE:
<223> OTHER INFORMATION: Synthetic Construct

<400> SEQUENCE: 7

```
cagctcgccc tgactcagcc tccctccgtg tctgggtctc ctggacagtc gatcaccatc    60
tcctgcactg gaaccagcag tgacgttggt ggttataact atgtctcctg gtaccaacaa   120
cacccagaaa gcccccaaac tcatgattta tgatgtcagt aatcggccct caggggtttc   180
taatcgcttc tctggctcca agtctggcaa cacggcctcc ctgacaatct ctgggctcca   240
ggctgaggac gagcgattat tactgctgct catatgcagg tagtagcact ttggtgttcg   300
gcggagggac caagctgacc gtcctaggtc agcccaaggc tgccccctcg gtcactctgt   360
tcccgccctc ctctgaggag cttcaagcca acaaggccac actggtgtgt ctcataagtg   420
acttctaccc gggccgtgac agtggcctgg aaggcagatg gcagcccgt caaggcggga    480
gtggagacca ccacaccctc caaacaaagc aacaacaagt acgcggccag cagctatctg   540
agcctgacgc ctgagcagga agtcccacag aagctacagc tgccaggtca cgcatgaagg   600
agcaccgtg gagaagacag tggcccctac agaatgt                              637
```

<210> SEQ ID NO 8
<211> LENGTH: 214
<212> TYPE: PRT
<213> ORGANISM: Artificial Sequence
<220> FEATURE:
<223> OTHER INFORMATION: Synthetic Construct

<400> SEQUENCE: 8

```
Gln Leu Ala Leu Thr Gln Pro Pro Ser Val Ser Gly Ser Pro Gly Gln
  1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Gly Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys
    210
```

<210> SEQ ID NO 9
<211> LENGTH: 671
<212> TYPE: DNA
<213> ORGANISM: Artificial Sequence
<220> FEATURE:
<223> OTHER INFORMATION: Synthetic Construct

<400> SEQUENCE: 9

```
gaggtgcagc tggtggagtc tggggctgag gtgaagaagc ctggggcctc agtgaaggtc      60
tcctgcaagg cttctggata caccttcacc agctatgata tcaactgggt gcgacaggcc     120
actggacggg cttgagtgga tgggatggat gaaccctaac agtggtaaca caggctatgc     180
acagaagttc cagggcagag tcaccatgac caggaacacc tccataagca cagcctacat     240
ggagctgagc agctagatct gaggacacgg ccgtgtatta ctgtgcgaga ggccgaggtt     300
ttgactggtt aaaaactttt gactactggg gccaggcac cctggtcacc gtctcccctg      360
cctccaccaa gggcccatcg tttccccctg gcaccctcct ccaagagcac ctctggggc      420
acagcggccc tgggctgcct ggtcaaggac tacttccccg aaccggtgac ggtgtcgtgg     480
aactcaggcg ccctgaccag cggcggcaac ttcccggct gtcctacagt cctcaggact      540
ctactccctc agcagcgtgg tgaccgtgcc ctccagcagc ttgggcaccc agacctacat     600
ctgcaacgtg aatcacaagc ccagcaacac caggtgacaa gaaagttgag cccaaatctt     660
gtgacaaaac t                                                         671
```

<210> SEQ ID NO 10
<211> LENGTH: 226
<212> TYPE: PRT
<213> ORGANISM: Artificial Sequence
<220> FEATURE:
<223> OTHER INFORMATION: Synthetic Construct

<400> SEQUENCE: 10

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Gly Phe Asp Trp Leu Lys Asn Phe Asp Tyr Trp Gly
            100                 105                 110

Gln Gly Thr Leu Val Thr Val Ser Pro Ala Ser Thr Lys Gly Pro Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr
225

<210> SEQ ID NO 11
<211> LENGTH: 12
<212> TYPE: PRT
<213> ORGANISM: Artificial Sequence
<220> FEATURE:
<223> OTHER INFORMATION: Synthetic Construct

<400> SEQUENCE: 11

Gly Ala Ser Gln Ser Val Ser Ser Ser Tyr Leu Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Gly Ala Ser Ser Arg Ala Thr Gly Ile Pro Asp
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic Construct

<400> SEQUENCE: 13

Tyr Gly Ser Ser Pro Pro Val Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Ser Tyr Asp Ile Asn
1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Trp Met Asn Pro Asn Ser Gly Asn Thr Gly Tyr Ala Gln Lys Phe Gln
1               5                   10                  15

Gly

```
<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Gly Lys Gly Ser Gly Tyr Tyr Asn Tyr
1               5

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Thr Gly Thr Ser Ser Asp Val Gly Gly Tyr Asn Tyr Val Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Asp Val Ser Asn Arg Pro Ser Gly Val Ser Asn
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Tyr Ala Gly Ser Ser Thr Leu Val
1               5

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct

<400> SEQUENCE: 20

Gly Arg Gly Phe Asp Trp Leu Lys Asn Phe Asp Tyr
1               5                   10

<210> SEQ ID NO 21
<211> LENGTH: 22
<212> TYPE: DNA
<213> ORGANISM: Artificial Sequence
<220> FEATURE:
<223> OTHER INFORMATION: Synthetic Construct

<400> SEQUENCE: 21
aagacagcta tcgcgattgc ag                                              22
```

```
<210> SEQ ID NO 22
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
acctattgcc tacggcagcc g                                              21
```

US 9,163,086 B2

METHODS AND COMPOSITIONS FOR THE TREATMENT OF PROLIFERATIVE AND PATHOGENIC DISEASES

CROSS-REFERENCE TO RELATED APPLICATIONS

This application is the National Stage of International Application No. PCT/US2010/45874, filed Aug. 18, 2010, which claims benefit to U.S. Provisional Application No. 61/234,918 filed Aug. 18, 2009.

This invention was made with government support under AI061174 awarded by National Institutes of Health. The government has certain rights in the invention.

BACKGROUND OF THE INVENTION

This invention relates to the treatment of proliferative and pathogenic diseases.

The complement regulatory protein CD59 is expressed on the surface of mammalian cells to protect host cells from the bystander effects of complement activation. CD59 activity inhibits formation of the membrane attack complex of complement (MAC) by binding to complement proteins C8 and C9 and preventing C9 incorporation and polymerization. During maturation by budding, a number of enveloped viruses, such as human *cytomegalovirus*, HCMV, human T-cell leukemia virus type 1 (HTLV-1), HIV-1, simian immunodeficiency virus, *Ebola* virus, influenza virus, and *vaccinia* virus, capture CD59 and use it to evade the complement system (Stoiber et al. Mol. Immunol. 42:153-160 (2005), Bernet et al. J Biosci 28:249-264 (2003), Rautemaa et al. Immunology 106:404-411 (2002), Nguyen et al. J Virol 74:3264-3272 (2000), Saifuddin et al. J. Exp. Med. 182:501-509 (1995), Spiller et al. J Infect Dis 176:339-347 (1997)). Other viruses, (e.g., Herpesvirus *saimiri*) express a CD59-like molecule that aids the virus in avoiding the complement system. Additionally, microbial parasites have been identified which also express a CD59-like molecule (e.g., *Naegleria fowleri* and *Schistosoma mansoni* (Parizade et al. J Exp Med 179:1625-1636 (1994), Fritzinger et al. Infect Immun 74:1189-1195 (2006))). These parasites, many of which are intracellular, are protected from human complement mediated lysis by CD59 and also use CD59 for infectivity (ibid).

Cancer is a disease marked by the uncontrolled growth of abnormal cells. Cancer cells have overcome the barriers imposed in normal cells, which have a finite lifespan, to grow indefinitely. As the growth of cancer cells continues, genetic alterations may persist until the cancerous cell has manifested itself to pursue a more aggressive growth phenotype. If left untreated, metastasis, the spread of cancer cells to distant areas of the body by way of the lymph system or bloodstream, may ensue, destroying healthy tissue.

CD59 is over-expressed in many cancer cells. Complement is a main mediator for antibody mediated cancer cytolysis. Up-regulation and high expression of CD59 can drive resistance to any antibody-mediated cancer therapy that activates complement as a component of its mechanism of activity. An example of resistance mediated by CD59 overexpression is resistance to the anti-CD20 chimeric MAb rituximab used for the treatment of B-cell non-Hodgkin lymphoma (B-NHL).

Accordingly, there exists a need for compounds and methods that sensitize pathogens and cancer cells to complement-mediated cell death.

SUMMARY OF THE INVENTION

In one aspect, the invention features a protein including an antibody, or a functional derivative thereof (e.g., a single chain antibody (scFv), a Fv, a Fab, a Fab', or a F(ab')$_2$), that binds hCD59, inhibits binding of hCD59 to complement proteins C8 and/or C9, and does not independently induce antibody-dependent cellular toxicity (ADCC), complement dependent cytolysis (CDC), or apoptosis. These proteins can bind the same epitope of hCD59 as ILYd4 and/or contain modifications that disrupt the independent induction of ADCC, CDC, and apoptosis.

In any of the foregoing aspects, the light chain variable domain of the antibody, or functional derivative thereof, includes at least one (e.g., two or three) of the following complementary determining regions (CDRs): a CDRL1 including the sequence of GASQSVSSSYLA (SEQ ID NO:11), a CDRL2 including the sequence of GASSRATGIPD (SEQ ID NO:12), and a CDRL3 including the sequence of YGSSPPVT (SEQ ID NO:13); and the heavy chain variable domain of the antibody, or functional derivative thereof, includes at least one (e.g., two or three) of the following CDRs: a CDRH1 including the sequence of SYDIN (SEQ ID NO:14), a CDRH2 including the sequence of WMNPNSGNTGYAQKFQG (SEQ ID NO:15), and a CDRH3 including the sequence of GKGSGYYNY (CDRH3; SEQ ID NO:16). In one embodiment, the antibody, or functional derivative thereof, has a light chain variable domain sequence as set forth in SEQ ID NO:4 (e.g., a sequence with 80%, 90%, 95%, 99%, or 100%, sequence identity of SEQ ID NO:4) and a heavy chain variable domain sequence as set forth in SEQ ID NO:6 (e.g., a sequence with 80%, 90%, 95%, 99%, or 100%, sequence identity of SEQ ID NO:6).

In another aspect, the light chain variable domain of the antibody, or functional derivative thereof, includes at least one (e.g., two or three) of the following complementary determining regions (CDRs): a CDRL1 including the sequence of TGTSSDVGGYNYVS (SEQ ID NO:17), a CDRL2 including the sequence of DVSNRPSGVSN (SEQ ID NO:18), and a CDRL3 including the sequence of YAGSSTLV (SEQ ID NO:19) and the heavy chain variable domain of the antibody, or functional derivative thereof, includes at least one (e.g., two or three) of the following CDRs: a CDRH1 including the sequence of SYDIN (SEQ ID NO:14), a CDRH2 including the sequence of WMNPNSGNTGYAQKFQG (SEQ ID NO:15), and a CDRH3 including the sequence of GRGFDWLKNFDY (SEQ ID NO:20). In one embodiment, the antibody, or functional derivative thereof, has a light chain variable domain sequence as set forth in SEQ ID NO:8 (e.g., a sequence with 80%, 90%, 95%, 99%, or 100%, sequence identity of SEQ ID NO:8) and a heavy chain variable domain sequence as set forth in SEQ ID NO:10 (e.g., a sequence with 80%, 90%, 95%, 99%, or 100%, sequence identity of SEQ ID NO:10).

In another aspect, the invention features a method for treating a proliferative disease (e.g., one in which neoplastic cells express hCD59) in a patient in need thereof, by administering to the patient any of the foregoing proteins and a therapeutic antibody (e.g., rituximab, MT201, 17-1A, herceptin, alemtuzumab, lym-1, bevacizumab, cetuximab, or IL-2 receptor alpha-directed monoclonal antibodies), wherein the protein of the invention and the therapeutic antibody are administered simultaneously (e.g., in the same formulation), or within 30 (e.g., 14) clays of each other, in amounts that together are sufficient to treat the proliferative disease.

In another aspect, the invention features a method for treating a pathogenic disease (e.g., a disease associated with a pathogen expressing CD59 or a CD59-like molecule) in a patient in need thereof, by administering to the patient any of the foregoing proteins. This method may further include administering a therapeutic antibody (e.g., a therapeutic antibody specific for a virus selected from human cytomegalovirus, HCMV, human T-cell leukemia virus type 1, HIV-1, simian immunodeficiency virus, *Ebola* virus, *Herpesvirus saimiri* virus, influenza virus, and *vaccinia* virus or a microbial parasite such as *Naegleria fowleri* and *Schistosoma manosni*), wherein the protein of the invention and the therapeutic antibody are administered simultaneously (e.g., in the same formulation), or within 30 (e.g., 14) days of each other, in amounts that together are sufficient to treat the pathogenic disease.

In yet another aspect, the invention features pharmaceutical compositions including any of the foregoing proteins and a pharmaceutically acceptable excipient.

In yet another aspect, the invention features kits including any of the foregoing proteins and a therapeutic antibody.

In certain embodiments, the protein is a substantially pure antibody.

By "patient" is meant any mammal, e.g., a human, mouse, pig, horse, dog, cat, or rat.

By "proliferative disease" is meant a disease featuring cell populations characterized by inappropriate accumulation in a tissue. This inappropriate accumulation may be the result of a genetic or epigenetic variation that occurs in one or more cells of the cell population. This genetic or epigenetic variation causes the cells of the cell population to grow faster, die slower, or differentiate slower than the surrounding, normal tissue. Examples of proliferative diseases are set forth herein.

By the "antibodies of the invention" is meant antibodies, or functional derivatives thereof, that possess ILYd4 activity.

By "CD59-like molecule" is meant a molecule expressed by a pathogen that binds domain 4 of the ILY polypeptide. Cells expressing CD59-like molecules are resistant to the lytic effect of complement by inhibiting complete formation of the membrane attack complex of complement.

By a "pathogen expressing CD59 or a CD59-like molecule" is meant a microbe (e.g., a virus, bacteria, or microbial parasite) that contains CD59 or a CD59-like molecule on its outer membrane. The term is meant to include viruses which capture CD59 molecules from host cells during the process of maturation by budding, as well as pathogens that contain genes encoding for CD59 or CD59-like molecules.

By "intermedilysin" or "ILY" is meant a polypeptide having the activity of a *Streptococcus intermedius* intermedilysin polypeptide. ILY can be purified from *Streptococcus intermedius* or can be produced recombinantly. An exemplary Genbank Accession number corresponding to the nucleic acid sequence of ILY is AB029317, and an exemplary Genbank Accession number corresponding to the polypeptide sequence of ILY is BAE16324.

By "domain 4 of ILY polypeptide," "ILY domain 4 polypeptide," or "ILYd4" is meant a protein containing a peptide sequence GALTLNHDGAFVARFYVYWEELGHDADGYETIRSRSWSGNGYNRGA HYSTTLRFKGNVRNIRVKVLGATGLAWEPWRLIYSKNDLPLVPQRNIS TWGTTLHPQFEDKVVKDNTD (SEQ ID NO:1) or RNIRVKVLGATGLAWEPWRLIYSKNDL-PLVPQRNISTWGTTLHPQFED KVVKDNTD (SEQ ID NO:2). This term explicitly excludes full length ILY.

By "fragment" is meant a portion of a polypeptide that contains, preferably, at least 10%, 20%, 30%, 40%, 50%, 60%, 70%, 80%, 90%, 95%, or more of the entire length of the polypeptide. A fragment may contain at least 10, 20, 30, 40, 50, 60, 70, 80, 90, 100, 110, or 114 amino acids or more.

By "ILY domain 4 activity" is meant the activity of a peptide that antagonizes human CD59 but does not directly cause substantial lysis of human red blood cells (RBCs) in the lysis assay described herein, does not independently cause complement dependent cytolysis (CDC), and does not independently cause antibody-dependent cellular cytotoxicity (ADCC) and apoptosis.

By "antagonism of hCD59" is meant a decrease of hCD59 binding to complement proteins C8 and/or C9, resulting in increased formation of the membrane attack complex of complement (MAC).

By "substantially pure antibody" is meant an antibody that has been separated from the components that naturally accompany it. Typically, the antibody is substantially pure when it is at least 60%, by weight, free from the proteins and naturally-occurring organic molecules with which it is naturally associated. Preferably the antibody is at least 75%, more preferably at least 90%, and most preferably at least 99%, by weight, pure.

An antibody is substantially free of naturally associated components when it is separated from those contaminants that accompany it in its natural state. Thus, an antibody that is chemically synthesized or produced in a cellular system different from the cell from which it naturally originates will be substantially free from its naturally associated components. Accordingly, substantially pure antibodies include those derived from eukaryotic organisms but synthesized in *E. coil* or other prokaryotes.

By "therapeutic antibody" is meant an antibody, or functional derivatives thereof, for the treatment of a proliferative or pathogenic disease.

The "percent sequence identity" of two nucleic acid or polypeptide sequences can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, Academic Press, 1987; and Sequence Analysis Primer, Gribskov, and Devereux, eds., M. Stockton Press, New York, 1991; and Carillo and Lipman, SIAM J. Applied Math. 48:1073, 1988.

Methods to determine identity are available in publicly available computer programs. Computer program methods to determine identity between two sequences include, but are not limited to, the GCG program package (Devereux et al., Nucleic Acids Research 12:387, 1984), BLASTP, BLASTN, and FASTA (Altschul et al., J. Mol. Biol. 215:403, 1990). The well known Smith Waterman algorithm may also be used to determine identity. The BLAST program is publicly available from NCBI and other sources (BLAST Manual, Altschul, et al., NCBI NLM NIH Bethesda, Md. 20894). Searches can be performed in URLs such as the following: http://www.ncbi.nlm.nih.gov/BLAST/unfinishedgenome.html; or http://www.tigr.org/cgi-bin/BlastSearch/blast.cgi. These software programs match similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains.

Common structural features among the variable regions of antibodies, or functional fragments thereof, are well known in the art. The DNA sequence encoding a particular antibody can generally be found following well known methods such as those described in Kabat, et al. 2987 *Sequence of Proteins of Immunological Interest* U.S. Department of Health and Human Services, Bethesda Md., which is incorporated herein as a reference. In addition, a general method for cloning functional variable regions from antibodies can be found in Chaudhary, V. K., et al., 1990 Proc. Natl. Acad. Sci. USA 87:1066, which is incorporated herein as a reference.

DETAILED DESCRIPTION

In general, the invention features proteins including an antibody, or functional derivatives thereof, that bind hCD59 and have the activity of domain 4 of the *Streptococcus intermedius* intermedilysin (ILY) protein. The following description focuses on antibodies and functional derivatives but is also generally applicable to recombinant proteins (e.g., fusion proteins) including the antibodies and functional derivatives, unless otherwise noted. In order to prevent the independent induction of CDC and ADCC, the antibodies of the invention can bind the same hCD59 epitope as ILYd4 and/or contain modifications that disrupt the interaction between the antibody and complement.

The antibodies of the invention antagonize hCD59 by decreasing the human CD59 binding to complement proteins C8 and/or C9, resulting in increased formation of MAC. Furthermore, the antibodies of the invention do not cause apoptosis or cell death of cells absent the binding of a second antibody to the cells. The second antibody can be a therapeutic antibody, or it can be a natively produced antibody.

I. Antibodies of the Invention

The invention features proteins, such as antibodies, and functional derivatives thereof, that bind hCD59 with ILYd4 activity. The development of antibodies is well understood in the art. In particular, the antibodies of the invention antagonize hCD59 without independently inducing apoptosis or ADCC. Such antibodies can be modified so that they do not directly interact with complement. For example, the antibodies might lack the Fc region (e.g., Fabs), or the Fc region can be modified (e.g., through mutation) not to interact with complement.

Two Fabs were identified that compete with ILYd4 for binding to hCD59, each of which is set forth below.

Fab-2 Clone3

VL-CL (Nucleic Acid)

(SEQ ID NO: 3)

5'-gagctcgtgttgacgcagtctccagccaccctgtctttgtctcca ggggaaagagccaccctctcctgcggggccagtcagagtgtcagcagc agctacttagcctggtaccagcagaaacctggccgctcccaggctcct catctatggtgcatccagcagggccactggcatcccagacaggttcag tggcagtgggtctgggacagacttcactctcaccatcagcagactgga gcctgaagattttgcattattactgtcagcagtatggtagctcacctc cagtcaccttcggccaagggacacgactggagattaaacgaactgtgg ctgcaccatctgtcttcatcttcccgccatctgatgagcagttgaatc ggaactgcctctgttgtgtgcctgctgaataacttctatcccagagag gccaaagtacagtggaaggtggataacgccctccaatcgggtaactcc caggagagtgtcacagagcaggacagcaggaagcacctacagcctcag cagcaccctgacgctgagcaaagcagactacgagaaacacaaagtcta -continued cgcctgcgaagtcacccatcagggcctgagcttgcccgtcacaaagag cttcaacagggagatgt-3'

VL-CL (Amino acid)

(three CDRs underlined; variable region in boldface)

(SEQ ID NO: 4)

ELVLTQSPATLSLSPGERATLSCGASQSVSSSYLAWYQQKPGQAPR

LLIYGASSRATGIPDRFSGSGSGTDFTLTISRLEPEDFAVYYCQQYGS

SPPVTFGQGTRLEIKRTVAAPSVFIFPPSDEQLSGTASVVCLLNNFYPR

EAKVQWKVDNALQSGNSQESVTEQDSKDSTYSLSSTLTLSKADYEKH

KVYACEVTHQGLSLPVTKSFNRGEC

VH-CH1 (Nucleic Acid)

(SEQ ID NO: 5)

5'-aaggtgcagctggtggagtctggggctgaggtgaagaagcctggg gcctcagtgaaggtctcctgcaaggcttctggatacaccttcaccagt tatgatatcaactgggtgcgacaggccactggacgggcttgagtggat gggatggatgaaccctaacagtggtaacacaggctatgcacagaagtt ccagggcagagtcaccatgaccaggaacacctccataagcacagccta catggagctgagcagctagatctgaggacacggccgtgtattactgtg cgagaggcaaagggagtggttattataactactggggccagggcaccc tggtcaccgtctcctctgcctccaccaagggcccatcggtatcccctg caccctcctccaagagcacctctgggggcacagcggccctgggctgcc tggtcaaggactacttccccgaaccggtgacggtgtcgtggaactcag gcgccctgaccagcggcgtgcacacctcccgctgtcctacagtcctca ggactctactccctcagcagcgtggtgaccgtgccctccagcacttgg gcacccagacctacatctgcaacgtgaatcacaagcccagcaacacca aggtggacagaagttgagcccaaatcttgtgacaaaactagt-3'

VH-CH1 (Amino Acid)

(three CDRs underlined; variable region in boldface)

(SEQ ID NO: 6)

KVQLVESGAEVKKPGASVKVSCKASGYTFTSYDINWVRQATGQGL

EWMGWMNPNSGNTGYAQKFQGRVTMTRNTSISTAYMELSSLRSE

DTAVYYCARGKGSGYYNYWGQGTLVTVSSASTKGPSVFLAPSSKST

SGGTAALGCLVKDYFPEPVTVSWNSGALTSGVHTFPAVLQSSGLYSLS

SVVTVPSSSLGTQTYICNVNHKPSNTKVDKKVEPKSCDKTS

Fab-3 Clone 7

VL-CL (Nucleic Acid)

(SEQ ID NO: 7)

5'-cagctcgccctgactcagcctccctccgtgtctgggtctcctgga cagtcgatcaccatctcctgcactggaaccagcagtgacgttggtggt tataactatgtctcctggtaccaacaacacccagaaagcccccaaact catgatttatgatgtcagtaatcggccctcaggggtttctaatcgctt -continued
```
ctctggctccaagtctggcaacacggcctccctgacaatctctgggct ccaggctgaggacgagcgattattactgctgctcatatgcaggtagta gcactttggtgttcggcggagggaccaagctgaccgtcctaggtcagc ccaaggctgcccctcggtcactctgttcccgcctcctctgaggagc ttcaagccaacaaggccacactggtgtgtctcataagtgacttctacc cgggccgtgacagtggcctggaaggcagatggcagccccgtcaaggcg ggagtggagaccaccacaccctccaaacaaagcaacaacaagtacgcg gccagcagctatctgagcctgacgcctgagcaggaagtcccacagaag ctacagctgccaggtcacgcatgaagggagcaccgtggagaagacagt ggcccctacagaatgt-3'
```

VL-CL (Amino Acid)
(three CDRs underlined; variable region in boldface)

(SEQ ID NO: 8)
QLALTQPPSVSGSPGQSITISC<u>TGTSSDVGGYNYVS</u>WYQQHPGKAP

KLMIY<u>DVSNRPSGVSNRF</u>SGSKSGNTASLTISGLQAEDEADYYCCS<u>Y</u>

<u>AGSSTLV</u>FGGGTKLTVLGQPKAAPSVTLFPPSSELQANKATLVCLISD

FYPGAVTVAWKADGSPVKAGVETTTPSKQSNNKYAASSYLSLTPEQW

KSHRSYSCQVTHEGSTVEKTVAPTEC

VH-CH1 (Nucleic Acid)

(SEQ ID NO: 9)
```
5'-gaggtgcagctggtggagtctggggctgaggtgaagaagcctggg gcctcagtgaaggtctcctgcaaggcttctggatacaccttcaccagc tatgatatcaactgggtgcgacaggccactggacgggcttgagtggat gggatggatgaaccctaacagtggtaacacaggctatgcacagaagtt ccagggcagagtcaccatgaccaggaacacctccataagcacagccta catggagctgagcagctagatctgaggacacggccgtgtattactgtg cgagaggccgaggttttgactggttaaaaaactttgactactggggcc agggcaccctggtcaccgtctccctgcctccaccaagggcccatcgt ttccccctggcaccctcctccaagagcacctctggggcacagcggcc ctgggctgcctggtcaaggactactccccgaaccggtgacggtgtcg tggaactcaggcgccctgaccagcggcggcaaccttcccggctgtcct acagtcctcaggactctactccctcagcagcgtggtgaccgtgccctc cagcagcttgggcacccagacctacatctgcaacgtgaatcacaagcc cagcaacaccaggtgacaagaaagttgagcccaaatcttgtgacaaaa ct-3'
```

VH-CH1 (Amino Acid)
(three CDRs underlined; variable region in boldface)

(SEQ ID NO: 10)
EVQLVESGAEVKKPGASVKVSCKASGYTFT<u>SYDIN</u>WVRQATGQGL

EWMG<u>WMNPNSGNTGYAQKFQG</u>RVTMTRNTSISTAYMELSSLRSE

DTAVYYCAR<u>GRGFDWLKNFDY</u>WGQGTLVTVSPASTKGPVFPLAPSS

KSTSGGTAALGCLVKDYFPEPVTVSWNSGALTSGVHTFPAVLQSSGLY

SLSSVVTVPSSSLGTQTYICNVNHKPSNTKVDKKVEPKSCDKT

The invention, in addition to featuring the above Fabs, also features methods of producing these Fabs using, e.g., plasmids and host cells containing, e.g., nucleic acids with the sequences of SEQ ID NOs: 3, 5, 7, and 9). Additionally, the invention features antibodies, or functional fragments thereof that contain at least one (e.g., 2, 3, 4, 5, or preferably 6) of the CDRs of the Fab-2 and Fab-3 proteins set forth above. These methods are discussed in more detail below.

Murine myeloma cell lines useful for the production of monoclonal antibodies can be obtained, for example, from the American Type Culture Collection (ATCC; Manassas, Va.). Human myeloma and mouse-human heteromyeloma cell lines have also been described (Kozbor et al., *J. Immunol.,* 133:3001-3005, 1984; Brodeur et al., Monoclonal Antibody Production Techniques and Applications, Marcel Dekker, Inc., New York, pp. 51-63, 1987).

The antibody may be prepared in any mammal, including mice, rats, rabbits, goats, camels, and humans. The antibody may be a member of one of the following immunoglobulin classes: IgG, IgM, IgA, IgD, or IgE, and the subclasses thereof, and preferably is an IgG antibody. While the preferred animal for producing monoclonal antibodies is mouse, the invention is not so limited; in fact, human antibodies may be used and may prove to be preferable. Such antibodies can be obtained by using human hybridomas (Cole et al., Monoclonal Antibodies and Cancer Therapy, Alan R. Liss Inc., p. 77-96, 1985). In the present invention, techniques developed for the production of chimeric antibodies by splicing the genes from a mouse antibody molecule of appropriate antigen specificity together with genes from a human antibody molecule can be used (Morrison et al., *Proc. Natl. Acad. Sci.* 81, 6851-6855, 1984; Neuberger et al., *Nature* 312, 604-608, 1984; Takeda et al., *Nature* 314, 452-454, 1985).

The invention also includes antibody functional derivatives that have ILYd4 activity. Functional derivatives include polypeptides with amino acid sequences substantially identical to the amino acid sequence of the variable or hypervariable regions of an antibody of the invention. Functional derivatives have antigen binding characteristics comparable to those of the antibodies, and include, for example, chimeric, humanized, fully human, and single chain antibodies or antibody fragments, antigen-binding antibody fragments, and antibodies fused to a second protein, or otherwise derivatized as is known in the art. Methods of producing such functional derivatives are disclosed, for example, in PCT Publication No. WO93/21319; European Patent No. 0 239 400 B1; PCT Publication No. WO89/09622; European Patent Application No. 0338,745; European Patent Application No. 0332424; U.S. Pat. No. 4,816,567; Morrison et al., *Proc. Natl. Acad. Sci. USA,* 81:6851-6855, 1984; Boulianne et al., *Nature,* 312: 643-646, 1984; Neuberger et al., *Nature,* 314:268-270, 1985, Smith et al., *FASEB J* 19:331-341 (2005); and U.S. Patent Application Publication Nos. 20050208043 and 20050276802, each of which is hereby incorporated by reference.

Chimeric antibodies preferably have constant regions derived substantially or exclusively from human antibody constant regions and variable regions derived substantially or exclusively from the sequence of the variable region from a mammal other than a human. Methods for humanizing non-human antibodies are well known in the art (for reviews see Vaswani and Hamilton, *Ann. Allergy Asthma Immunol.,*

81:105-119, 1998 and Carter, *Nature Reviews Cancer,* 1:118-129, 2001). Generally, a humanized antibody has one or more amino acid residues introduced into it from a source that is non-human. These non-human amino acid residues are often referred to as import residues, which are typically taken from an import variable domain. Humanization can be essentially performed following the methods known in the art (Jones et al., *Nature,* 321:522-525, 1986; Riechmann et al., *Nature,* 332:323-329, 1988; and Verhoeyen et al., *Science,* 239:1534-1536 1988), by substituting rodent CDRs or other CDR sequences for the corresponding sequences of a human antibody. Accordingly, such humanized antibodies are chimeric antibodies wherein substantially less than an intact human variable domain has been substituted by the corresponding sequence from a non-human species (see for example, U.S. Pat. No. 4,816,567). In practice, humanized antibodies are typically human antibodies in which some CDR residues and possibly some FR residues are substituted by residues from analogous sites in rodent antibodies (Presta, *Curr. Op. Struct. Biol.,* 2:593-596, 1992).

Additional methods for the preparation of humanized antibodies can be found in U.S. Pat. Nos. 5,821,337, and 6,054,297, and Carter, (supra) which are all incorporated herein by reference. The humanized antibody is selected from any class of immunoglobulins, including IgM, IgG, IgD, IgA and IgE, and any isotype, including $IgG_1$, $IgG_2$, $IgG_3$, and $IgG_4$. Where cytotoxic activity is not needed, such as in the present invention, the constant domain is preferably of the $IgG_2$ class. The humanized antibody may comprise sequences from more than one class or isotype, and selecting particular constant domains to optimize desired effector functions is within the ordinary skill in the art.

Human antibodies can also be produced using various techniques known in the art, including phage display libraries (Marks et al., *J. Mol. Biol.,* 222:581-597, 1991, Winter et al. *Annu. Rev. Immunol.,* 12:433-455, 1994, and Smith et al., supra). The techniques of Cole et al. and Boerner et al. are also useful for the preparation of human monoclonal antibodies (Cole et al., supra; Boerner et al., *J. Immunol.,* 147: 86-95, 1991).

Suitable mammals other than a human include any mammal from which monoclonal antibodies may be made. Examples of mammals other than a human include, for example a rabbit, rat, mouse, horse, goat, or primate; a mouse is preferred.

"Functional derivatives" of antibodies include single-chain antibody fragments, also known as single-chain antibodies (scFvs). Single-chain antibody fragments are recombinant polypeptides which typically bind antigens or receptors; these fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the $V_L$ and $V_H$ domains occurs once they are linked so as to maintain the target molecule binding-specificity of the whole antibody from which the single-chain antibody fragment is derived. Generally, the carboxyl terminus of the $V_L$ or $V_H$ sequence is covalently linked by such a peptide linker to the amino acid terminus of a complementary $V_L$ and $V_H$ sequence. Single-chain antibody fragments can be generated by molecular cloning, antibody phage display library or similar techniques. These proteins can be produced either in eukaryotic cells or prokaryotic cells, including bacteria.

Single-chain antibody fragments contain amino acid sequences having at least one of the variable regions or CDRs of the whole antibodies described in this specification but are lacking some or all of the constant domains of those antibodies. These constant domains are not necessary for antigen binding but constitute a major portion of the structure of whole antibodies. Single-chain antibody fragments may therefore overcome some of the problems associated with the use of antibodies containing part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient.

"Functional derivatives" further include fragments of antibodies that have the same or comparable binding characteristics to those of the whole antibody. Such fragments may contain one or both Fab fragments or the $F(ab')_2$ fragment (e.g., Fv, Fab, Fab', $F(ab')_2$ or other antigen-binding subsequences of antibodies). Preferably the antibody fragments contain all six CDRs of the whole antibody, although fragments containing fewer than all of such regions, such as three, four or five CDRs, may also be functional.

Further, the functional derivatives may be or may combine members of any one of the following immunoglobulin classes: IgG, IgM, IgA, IgD, or IgE, and the subclasses thereof.

Derivatives of antibodies are prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody.

DNA encoding chimeric antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the CDRs derived substantially or exclusively from the corresponding human antibody regions and DNA encoding CDRs derived substantially or exclusively from a mammal other than a human.

Suitable sources of DNA molecules that encode fragments of antibodies include cells, such as hybridomas, that express the full-length antibody. The fragments may be used by themselves as antibody derivatives, or may be recombined into derivatives, as described above.

The following methods are used to identify antibodies, and functional derivatives thereof, of the invention.

Antibodies of the invention can bind the same epitope as ILYd4.

Erythrocytes from humans or hCD59RBC transgenic mice that specifically express only human CD59 are pre-incubated with a candidate antibody (for 10 minutes at room temperature) then incubated with ILYd4, or mouse anti-hCD59 monoclonal antibody (0.2 µg/ml) (BRIC 229, Bristol, Great Britain) at room temperature for 30 minutes followed by washing. The cells are further incubated with FITC-conjugate anti-His antibody or a FITC-conjugated corresponding secondary antibody, respectively. The cells are washed with PBS three times followed by measuring the fluorescence intensity using a FACScan (Becton Dickinson, Franklin Lakes, N.J.). Cells pre-incubated with antibodies of the invention that bind to the same epitope as ILYd4 do not stain with either ILYd4 plus FITC anti-HIS or BRIC 229 plus FITC secondary antibody. Cells not pre-incubated with an antibody of the invention only stain with BRIC 229 plus FITC secondary antibody. Antibodies of the invention can functionally interact with the same epitope of hCD59 as ILYd4.

Erythrocytes from humans or hCD59RBC transgenic mice are pre-incubated with a candidate antibody and ILYd4 (in different concentrations) at room temperature for 10 minutes. Full length ILY is added to induce hemolysis. Antibodies of the invention block full length ILY-mediated hemolysis, and therefore, functionally block ILY access to human CD59 in the cells.

Antibodies of the invention induce complement-mediated lysis in human erythrocytes.

The sensitivity of human erythrocytes to human complement-mediated lysis in the presence or absence of a candidate antibody compared to ILYd4 is assessed by two methods: (1) cobra venom factor (CVF, 5 mg/L) lysis assay; and (2) anti-human erythrocyte antibody (Ab)-sensitized erythrocyte method, as described in Hu et al. *Nat Med* 14:98-103 (2008), which is hereby incorporated by reference in its entirety. Human serum (HS, 50% v/v) is used as a source of complement, and heat-inactivated human serum (HIS, 50%, v/v) is used as a control. Combined with the anti-human erythrocyte antibody, antibodies of the invention enhance complement-mediated lysis to a similar degree as ILYd4. Furthermore, when tested alone, antibodies of the invention do not induce hemolysis.

Antibodies of the invention do not alone cause apoptosis.

Candidate antibodies are incubated with hCD59 expressing FL lymphoma cells for 48 hours, and apoptosis is assessed (e.g., using terminal nucleotidyl transferase-mediated nick end labeling (TUNEL) assays (Roche) according to the manufacturer's instructions). Similarly to ILYd4, the antibodies of the invention do not induce apoptosis in this assay.

Antibodies of the invention do not alone cause ADCC.

FL lymphoma cells are stained with the green fluorescence cytoplasmic dye 5- and (6)-carboxyfluorescein diacetate, succinimidylester (CSFE; Molecular Probes, Inc.). After washing, labeled-FL cells are incubated with either a candidate antibody or ILYd4. Peripheral blood mononuclear effector (E) cells (PBMCs) are mixed with target (T) cells at 50:1 E/T cell ratio and incubated for 4 hours at 37° C. in 5% $CO_2$. The cells are centrifuged and assayed for dye release with Infinite F200 (Tecan). The percentage of specific lysis is determined as: [(test release–spontaneous release)/(total release–spontaneous release)]×100. Dead cells will be stained with propidium iodide (50 Ag/mL; Sigma-Aldrich) and analyzed on a FACScalibur instrument to control the data obtained by measuring dye release. Similarly to ILYd4, the antibodies of the invention will not alone induce ADCC.

Additional experimental methods for measuring ILYd4 activity are described, e.g., in International Application Nos. PCT/US2008/004191 and PCT/US2008004193, each of which is incorporated by reference in their entirety.

II. Methods of Administration

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and the patient response to the treatment. Additionally, a person having a greater risk of developing a proliferative or pathogenic disease may receive treatment to inhibit or delay the onset of symptoms.

Routes of administration for the various embodiments include, but are not limited to, topical, transdermal, transcranial, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all nondermal routes of administration, and specifically excludes topical and transdermal routes of administration.

The antibodies of the invention may be administered orally in the form of tablets, capsules, elixirs, or syrups, or rectally in the form of suppositories. The antibodies may also be administered topically in the form of foams, lotions, drops, creams, ointments, emollients, or gels. Parenteral administration of a compound is suitably performed, for example, in the form of saline solutions or with the compound incorporated into liposomes.

Dosages

The dosage of the antibody of the invention depends on several factors, including: the administration method, the disease to be treated, the severity of the disease, whether the disease is to be treated or prevented, and the age, weight, and health of the person to be treated. Additionally, pharmacogenomic (the effect of genotype on the pharmacokinetic, pharmacodynamic, or efficacy profile of a therapeutic) information about a particular patient may affect the dosage used.

Continuous daily dosing with an antibody of the invention may not be required. A therapeutic regimen may require cycles, during which time an antibody is not administered, or therapy may be provided on an as needed basis during periods of acute disease. The appropriate dosage and treatment regimen can be determined by one skilled in the art.

III. Indications

The antibodies of the invention are useful for treating any disease characterized by undesired hCD59 activity.

The antibodies of the invention are useful for the treatment of cancers and other disorders characterized by hyperproliferative cells (proliferative diseases). In these embodiments, the antibodies of the invention can be administered directly to a CD59-expressing neoplasia, or systemically to a subject having a neoplasia. Preferably, the antibodies of the invention will be administered with an anti-cancer therapeutic antibody.

In a separate embodiment, an antibody of the invention can be administered to a patient diagnosed with a proliferative disorder that is not characterized by the cell surface expression of CD59. Here, the compounds are administered in conjunction with an anti-cancer therapeutic antibody to prevent resistance to the therapeutic antibody based treatment.

Antibody therapy may be performed alone or in conjunction with another therapy (e.g., surgery, radiation therapy, chemotherapy, immunotherapy, anti-angiogenesis therapy, or gene therapy). Therapy may be given in on-and-off cycles that include rest periods so that the patient's body has a chance to recovery from any as yet unforeseen side-effects.

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, and multiple myeloma), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

The antibodies of the invention are also useful for the treatment of pathogens characterized by expression of CD59 or CD59-like molecules. For example, the antibodies of the invention are useful to treat viruses containing CD59 in their envelope, where the CD59 is captured during maturation by budding from a host cell expressing CD59 (e.g., human cytomegalovirus, HCMV, human T-cell leukemia virus type 1, HIV-1, simian immunodeficiency virus, *Ebola* virus, influenza virus, and *vaccinia* virus (a poxvirus) (Stoiber et al. Mol. Immunol. 42:153-160 (2005), Bernet et al. J Biosci 28:249-264 (2003), Rautemaa et al. Immunology 106:404-411 (2002), Nguyen et al. J Virol 74:3264-3272 (2000), Saifuddin et al. J. Exp. Med. 182:501-509 (1995), Spiller et al. J Infect Dis 176:339-347 (1997))). The antibodies of the invention are also useful for the treatment of patients infected with parasites or viruses that directly express CD59 or a CD59-like molecule, such as Herpesvirus *saimiri* virus, *Schistosoma manosni*, and *Naegleria fowleri* (Parizade et al. J Exp Med 179:1625-1636 (1994), Fritzinger et al. Infect Immun 74:1189-1195 (2006)). In these embodiments, an antibody of the invention can be administered directly to a tissue infected with a pathogen or systemically to a subject infected with a pathogen. Preferably, the antibody of the invention will be administered with an antibody specific for the CD59- or CD59-like expressing pathogen. Therapy may be performed alone or in conjunction with other anti-microbial therapies.

IV. Therapeutic Antibodies

The invention features the treatment of proliferative or pathogenic diseases through the administration of the antibodies of the invention in combination with a therapeutic antibody. Administration of the antibodies of the invention may sensitize the cells targeted by antibody therapy to complement-mediated cell lysis. Examples of therapeutic antibodies for use in the methods of the invention for treating proliferative disorders are set forth in Table 1.

TABLE 1

Relevant antibodies that are applied for cancer therapy

| Antibody name | Target antigen | Cancer |
|---|---|---|
| Rituximab | CD20 | B-cell lymphomas |
| MT201 and 17-1A | Ep-CAM | Colorectal and breast cancer |
| Herceptin | HER2 | Breast cancer and lymphomas |
| Alemtuzumab | CD52 | Chronic lymphocytic leukemia |
| Lym-1 | HLA-DR | Lymphoma |
| Bevacizumab | VEGF | Cancer of the colon or rectum |
| IL-2Rα-directed monoclonal antibodies | | T-cell leukemia |
| Alemtuzumab | CD52 | CLL |
| Panitumumab | EGFR | Colorectal cancer |
| Cetuximab | EGFR | Colorectal cancer, head and neck cancer |

Examples of therapeutic antibodies for use in the methods of the invention for treating HIV are the humanized antibody hNM-01 (Nakamura et al., Hybridoma, 19:427 (2000)), and the humanized KD-247 antibody (Matsushita et al., Hum Antibodies 14:81-88 (2005)). An example for treating RSV is Palivizumab. Other antibodies (preferably humanized antibodies) can be developed using any epitope of HIV or other CD59-expressing pathogen using standard methods.

In addition to the antibodies and indications listed above, the invention features co-administration of the antibodies of the invention in combination with any treatment that would be enhanced by inhibition of human CD59 activity.

V. Experimental Results

A human naive Fab library was screened against immobilized CD59. The binding of selected Fab to CD59 was tested for inhibition by D408Y (ILY domain 4 protein). Initially, plates were coated D408Y, CD59 was added, and the interaction D408Y and CD59 was detected using a specific anti-CD59 antibody. Subsequently, the first three rounds of screening were performed by directly coating CD59 and the $4^{th}$ round of screening was performed by coating lysed CD59-epressing-red blood cells. From the $4^{th}$ eluate, 40 clones were identified and phage ELISA was performed using plates coated with CD59. Subsequently, 32 positive clones were identified. Three unique Fabs (Fab-1, 2, and 3) were revealed by DNA sequencing from 32 positive clones. Meanwhile, another three Fabs (Fab 4,5, and 6) were also identified from negative clones. Since there are un-expected internal 'TAG' amber stop codons within the genes of Fab-1 and Fab-6, 4 Fabs (Fabs 2, 3, 4, and 5) were subjected to soluble expression and soluble ELISA. The binding signals of two of the positive clones (clone 3 and 7; identified as Fab-2 and Fab-3, respectively) in the presence of CD59 were studied. The amino acid sequences for the variable domain heavy and light chains for Fab-2 and Fab-3 are set forth above.

Materials and Reagents

Target protein: CD59

Ligand: D408Y (ILY domain 4 protein)

Anti-CD59 antibody

Two tubes of red blood cells

Pre-made human naïve Fab library (HuFabL)

M13K07 helper phage

Anti-HA mAb-HRP conjugate

Sequencing primers:

(VL-primer); 5'-AAGACAGCTATCGCGATTGCAG-3' (SEQ ID NO:21)

(VH-primer): 5'-ACCTATTGCCTACGGCAGCCG-3' (SEQ ID NO:22)

LB Medium: Per liter: 10 g Bacto-Tryptone, 5 g yeast extract, 5 g NaCl.

LB Plates: LB medium+15 g/L agarose.

2TY medium: 16 g/L tryptone, 10 g/L yeast extract, 5 g/L NaCl, made up to 1 L in deionized $H_2O$, and adjusted to pH 7.0 with 1 M NaOH. Autoclave.

2TY-G: 2TY containing 1% (w/v) glucose

2TY-AG: 2TY containing 100 μg/mL ampicillin (AMP) and 1% (w/v) glucose

2TY-A: 2TY containing 100 μg/mL ampicillin (AMP)

2TY-AK: 2TY containing 100 μg/mL ampicillin, 50 μg/mL kanamycin TYE agar plates: Add 15 g agar to 1 L 2TY medium, autoclave, when cool, add glucose to 1% (w/v) and AMP.

PBS: Per liter: 8 g NaCl, 0.2 g KCl, 1.7 g Na2HPO4, 0.163 g KH2PO4, pH to 7.4 with HCl.

Blocking buffer: 0.1 M NaHCO3 (pH 8.6), 5 mg/mL BSA, 0.02% NaN3, 0.1 μg/mL streptavidin. Filter sterilize, store at 4° C.

Coating Buffer: 0.1 M NaHCO3 (pH 8.6).

Acidic eluting buffer: 0.2 M Glycine-HCl (pH2.2), 1 mg/mL BSA.

Phage precipitant (PEG/NaCl): 20% (w/v) polyethylene glycol-8000, 2.5 M NaCl. Autoclave, store at room temperature.

TE buffer: 10 mM Tris-HCl (pH 8.0), 1 mM EDTA.

50% glycerol/PBS: Equal mix of PBS and Glycerol.

HRP-conjugated anti-M13 antibody.

Substrate of HRP: OPD from Sigma.

Substrate buffer: 2.6 g Citric acid and 6.9 g Na2HPO4 up to 500 mL. Adjust pH to 5.0 if needed.

Experimental Procedure:

1. Prepared M13KO7 Helper Phage

Prepared helper phage by infecting log-phase TG1 bacterial cells with M13K07 phage at different dilutions for 30 min at 37° C. and plated in top agar onto 2TY plates.

Inoculated a small plaque in 3 mL liquid 2TY medium. Added 30 μL overnight culture of TG1 and grow for 2 hours at 37° C.

Diluted the culture in 1 L 2TY medium and grow for 1 hour. Added kanamycin to 50 μg/mL and grow for 16 hours at 37° C.

Removed cells by centrifugation (10 min at 5000 g) and precipitated phage from the supernatant by addition of 0.25 vols of phage precipitant. After 30 min incubation on ice, collected the phage particles by centrifugation during 10 min at 5000 g. Resuspended the pellet in 5 mL PBS and sterilized through a 0.22 μm filter.

Titrated the helper phage by determining the number of plaque-forming units (pfu) on 2TY plates with top-agar layers containing 100 μL TG1 (saturated culture) and dilutions of phage. Diluted the phage stock solution to $1\times10^{13}$ pfu/mL and stored in small aliquots at −20° C.

2. Prepare Library Phages

Inoculated 500 mL 2TY-G with the library glycerol stock and incubate at 37° C., shaking, at 250 rpm until the optical density at 600 nm reached 0.8-0.9.

Added M13KO7 helper phage to a final concentration of $5\times10^9$ pfu/mL, and incubated for 30 min at 37° C. without shaking, followed by 30 min with gentle shaking (200 rpm), to allow phage infection.

Recovered the cells by centrifugation at 2200 g for 15 min and re-suspended the pellet in the same volume of 2TY-AK. Incubated overnight at 30° C. with rapid shaking (300 rpm).

Pelleted the cells by centrifugation at 7000 g for 15 min at 4° C. and recover the supernatant containing the phage into pre-chilled 1-L bottles.

Added 0.3 vols of phage precipitant. Mixed gently and allowed the phage to precipitate for 1 hour on ice.

Pelleted the phage by centrifugation twice at 7000 g for 15 min in the same bottle at 4° C. Removed as much of the supernatant as possible and re-suspended the pellet in 8 mL PBS.

Re-centrifuged the phage in smaller tubes at 12,000 g for 10 min and recovered the phage via the supernatant. Ensured that any bacterial pellet that appeared was left undisturbed.

Titered phage stocks by infecting TG1 cells with dilutions of phage stock, plated to 2TY-AG, incubated, and enumerated the ampicillin resistant colonies that appeared. The phage was then be stored in aliquots at 4° C. for screening.

3. Panning

Coated the target proteins directly by incubating at 37° C. for 2 hours.

Blocked panning plates (Nunc) with the blocking buffer at 4° C. overnight.

Washed blocked wells 6 times with 0.1% PBST (PBS with 0.1% Tween 20(V/V)).

Mixed equal volumes of the phage library and 4% PBSM (PBS containing 4% milk) and added into panning wells. Incubated at room temperature for 60 min.

Washed 10-20 times with PBSMT (PBS containing 2% milk, a certain percent of Tween-20).

Added 200 μL acidic eluting buffer and incubated 5 min at room temperature. Transferred the supernatant containing the phages to a new tube and neutralize with Tris-HCl buffer.

Infected a fresh exponentially growing culture of *Escherichia coli* TG1 with the eluted phages and amplified half of them for further rounds of selection. Stored the remaining eluate at 4° C.

4. Phage ELISA

1) Prepared Single Clones of Antibody-Displaying Phages

Inoculated single clones of the eluate from the $4^{th}$ round into 5 mL of 2YT-AG medium and incubated at 37° C. overnight.

Prepared the glycerol stock for each clone with the overnight culture. Inoculated 100 μL of overnight culture into 20 mL of 2YT-AG medium. Grew for a few hours at 37° C. until the optical density at OD600 reached 0.4-0.5.

Added VCSM13 helper phage at a multiplicity of infection of 20 (i.e., the number of phage particles/host cell). Infected the cells by incubating 30 min at 37° C. without shaking and another 30 min with shaking.

Collected infected cells by centrifugation (10 min at 5000 g). Re-suspended in 2YT-AK and grew the culture for 16 hours at 30° C.

Precipitated phage particles from the supernatant as described above. Re-suspended the phage pellet in 1 mL PBS and removed cellular debris by centrifugation (10 min at 5000 g).

To remove Ab fragments not associated to phage particles, carried out a second precipitation. Re-suspended the phage pellet in 250 μL PBS, clarified again by centrifugation.

2) Phage ELISA by coating the target proteins (CD59 or red cell membrane) directly.

Coated 100 μL target protein (10 μg/mL) in coating buffer by incubating at 4° C. overnight.

Shook out the coating solution and washed once with the washing buffer. Blocked all wells with 250 μL of blocking buffer. In order to test the binding of each selected sequence to BSA-coated plastic surface, enough uncoated wells were also blocked. Incubated the blocked plates 1-2 hours at 4° C.

Shook out the blocking buffer and washed the plate six times with the washing buffer.

Added 100 μL of phage solution in washing buffer per well. Incubated at room temperature for 1-2 hours.

Washed 6 times with the washing buffer. Diluted HRP-conjugated anti-M13 antibody (GE healthcare) 1:5,000 in blocking buffer. Added 100 μL of diluted conjugate per well and incubated at room temperature for 1 hour.

Washed 6 times with the washing buffer. Prepared the HRP substrate solution as follows: a stock solution of OPD can be prepared in advance by dissolving 22 mg OPD (Sigma) in 100 mL of 50 mM sodium citrate, pH 4.0. Filter-sterilize and store at 4° C. Immediately prior to the detection step, added 36 μL 30% $H_2O_2$ to 21 mL of OPD stock solution.

Added 100 μL of substrate solution per well and incubated at room temperature for 30 minutes.

Read plates using a microplate reader set at 490nm.

5. Soluble ELISA

Soluble expression in periplasm of HB2151 cells

Picked a single colony of HB2151 bacteria harboring the Fab expression vector from a LB plate and grew overnight at 37° C. in 2TY.

Added 100 μL HB2151 culture to 50 mL 2TY and grew at 37° C. (with shaking) to an OD600 of 0.6-0.8.

Infected HB2151 with phages of positive clones identified by phage ELISA. Inoculated 1 μL of phages into 200 μL aliquots of the log-phase HB2151 culture. Incubated for 30 min at 37° C. (no shaking). Plated onto LB-AG plates and incubated overnight at 37° C.

Inoculated a single colony into 5mL aliquot of 2TY growth medium and grew overnight at 37° C. (with gentle shaking).

Took a 250 μL aliquot of overnight culture from each well and transfer to 25 mL 2TY growth medium. Grew the cultures at 37° C. until OD600 is approx 0.6.

Added 250 μL 2TY induction medium and grow overnight at 30° C.

Collected cells via centrifugation at 3500 g for 10 min. Released soluble Fab by ultra-sonication of cell suspensions in 1/10 volume of PBS.

Centrifuged at 9000 g for 10 min and collected the supernatant containing soluble Fab.

2) Soluble Fab ELISA

Repeated steps outlined in 4-2.

Discarded the block solution and added 100 μL of supernatant containing soluble Fab. Incubated for 2 hours at room temperature.

Washed the wells 3× with 200 μL PBST.

Added 100 μL of PBSM diluted HRP conjugate of rabbit anti Human Fab polyclonal antibody to each well and incubate for 1 hour at room temperature.

Washed the wells 3× with 200 μL PBST.

Developed the HRP reaction using OPD and read optical density at 490 nM.

6. DNA Sequencing

Inoculated 2 μL glycerol stock TG1 bacterial cells harboring the plasmid for each positive clone (determined by phage ELISA and/or soluble ELISA) into 5 mL LB-A medium (LB medium added with 100 μg/mL ampicillin). Grew overnight at 37° C. with shaking.

Isolated plasmids for each positive clone from bacterial cells using a Plasmid Isolation Kit (e.g. Qiagen Miniprep kit).

Conducted DNA sequencing using "V1-primer" and "VH-primer" as the primers.

7. Bioinformatics Analysis

Translated returned sequences with professional software (Vector NTI®, Version 10). Aligned the protein sequences. Grouped the clones that encoded the same protein sequences.

Results

Validation of Interaction between CD59 and 0408Y

40 μg/mL D408Y was coated and 2.5-40 μg/mL CD59 added in a validation ELISA. As shown in Table 1, with 40 μg/mL CD59 a positive binding signal was observed. Therefore, 40 μg/mL CD59 was coated in the first round of screening.

TABLE 1

The result of validation ELISA

| CD59 (μg/mL) | OD490 |
|---|---|
| 40 | 0.203 |
| 20 | 0.075 |
| 10 | 0.054 |
| 5 | 0.05 |
| 2.5 | 0.048 |
| 0 | 0.048 |
| Direct coat 10 μg/mL CD59 | 0.644 |

The Panning:

As shown in the Table 2, only about 4,000 phages were eluted in the first round of screening. After 4 rounds of screening, the enriching effect was observed by reducing the enriching factor.

TABLE 2

Summarization of the panning process

| Round | Conditions | Input | Output | Enriching factor |
|---|---|---|---|---|
| 1st | Target protein: 40 μg/mL CD59 Washing: 10 times with 0.1% Tween-20 PBST Elution: acidic elution buffer | $1.7 \times 10^{12}$ | $4.8 \times 10^3$ | $3.5 \times 10^8$ |
| 2nd | Target protein: 40 μg/mL CD59 Washing: 10 times with 0.3% Tween-20 PBST Elution: acidic elution buffer | $7.1 \times 10^{12}$ | $6.9 \times 10^4$ | $1.0 \times 10^8$ |
| 3rd | Target protein: 40 μg/mL CD59 Washing: 10 times with 0.3% Tween-20 PBST Elution: acidic elution buffer | $1.2 \times 10^{12}$ | $4.3 \times 10^4$ | $2.8 \times 10^7$ |
| 4th | Target: 50 μg/mL lysed CD59-expressing-red-blood-cells Control: 50 μg/mL lysed non-CD59-expressing red-blood-cells Washing: 10 times with 0.3% Tween-20 PBST Elution: acidic elution buffer | $1.2 \times 10^{12}$ | $1.3 \times 10^5$ | $9.2 \times 10^6$ |

Notes:
Enriching factor = input/output

Phage ELISA 40 clones were randomly picked up from the 4th eluate and subjected to phage ELISA. As shown in Table 3, 32 positive clones were identified. When phage ELISA was conducted using membrane extracts of CD59 positive and negative red cells as antigens, the lower readings were observed for them in CD59 (−) wells than in CD59 (+) wells, as shown in Table 4.

TABLE 3

The result of the first phage ELISA

| Clone | Ag+ phage+ | Ag− phage+ |
|---|---|---|
| 1 | 0.206 | 0.071 |
| 2 | 0.236 | 0.063 |

TABLE 3-continued

The result of the first phage ELISA

| Clone | Ag+ phage+ | Ag− phage+ |
|---|---|---|
| 3 | 0.169 | 0.058 |
| 4 | 0.305 | 0.061 |
| 5 | 0.281 | 0.065 |
| 6 | 0.098 | 0.048 |
| 7 | 0.211 | 0.086 |
| 8 | 0.157 | 0.061 |
| 9 | 0.336 | 0.352 |
| 10 | 0.14 | 0.064 |
| 11 | 0.226 | 0.066 |
| 12 | 0.228 | 0.078 |
| 13 | 0.212 | 0.055 |
| 14 | 0.254 | 0.056 |
| 15 | 0.069 | 0.056 |
| 16 | 0.177 | 0.064 |
| 17 | 0.169 | 0.074 |
| 18 | 0.286 | 0.098 |
| 19 | 0.192 | 0.061 |
| 20 | 0.312 | 0.074 |
| 21 | 0.356 | 0.056 |
| 22 | 0.118 | 0.065 |
| 23 | 0.065 | 0.056 |
| 24 | 0.400 | 0.069 |
| 25 | 0.312 | 0.074 |
| 26 | 0.222 | 0.096 |
| 27 | 0.078 | 0.079 |
| 28 | 0.117 | 0.115 |
| 29 | 0.252 | 0.055 |
| 30 | 0.274 | 0.098 |
| 31 | 0.298 | 0.068 |
| 32 | 0.291 | 0.061 |
| 33 | 0.215 | 0.064 |
| 34 | 0.345 | 0.084 |
| 35 | 0.317 | 0.065 |
| 36 | 0.399 | 0.074 |
| 37 | 0.282 | 0.085 |
| 38 | 0.211 | 0.068 |
| 39 | 0.208 | 0.064 |
| 40 | 0.265 | 0.054 |
| M13KO7 | 0.046 | 0.046 |

TABLE 4

The result of the 2nd phage ELISA

| Clone | Ag+ phage+ CD59(+)red cell | Ag+ phage+ CD59(−)red cell | Ag− phage+ |
|---|---|---|---|
| 1 | 0.149 | 0.105 | 0.056 |
| 2 | 0.132 | 0.087 | 0.047 |
| 3 | 0.322 | 0.2 | 0.056 |
| 4 | 0.115 | 0.096 | 0.048 |
| 5 | 0.163 | 0.125 | 0.059 |
| 7 | 0.34 | 0.237 | 0.064 |
| 8 | 0.101 | 0.076 | 0.047 |
| 11 | 0.121 | 0.110 | |
| 12 | 0.141 | 0.134 | 0.044 |
| 13 | 0.125 | 0.112 | 0.054 |
| 14 | 0.132 | 0.105 | 0.065 |
| 16 | 0.122 | 0.106 | 0.064 |
| 17 | 0.133 | 0.121 | 0.054 |
| 18 | 0.111 | 0.095 | 0.044 |
| 19 | 0.106 | 0.098 | 0.065 |
| 20 | 0.125 | 0.114 | 0.045 |
| 21 | 0.152 | 0.117 | 0.042 |
| 24 | 0.100 | 0.085 | 0.044 |
| 25 | 0.171 | 0.154 | 0.054 |
| 26 | 0.112 | 0.105 | 0.045 |
| 29 | 0.114 | 0.095 | 0.058 |
| 30 | 0.151 | 0.122 | 0.061 |
| 31 | 0.166 | 0.118 | 0.062 |
| 32 | 0.132 | 0.101 | 0.046 |
| 33 | 0.154 | 0.099 | 0.049 |
| 34 | 0.113 | 0.099 | 0.081 |
| 35 | 0.210 | 0.141 | 0.075 |
| 36 | 0.222 | 0.184 | 0.057 |
| 37 | 0.211 | 0.165 | 0.057 |
| 38 | 0.109 | 0.143 | 0.071 |
| 39 | 0.124 | 0.117 | 0.064 |
| 40 | 0.141 | 0.115 | 0.058 |
| M13KO7 | 0.046 | 0.046 | 0.044 |

DNA Sequencing 32 positive clones were DNA sequenced and three unique Fab sequences (Fab-1, 2, and 3) were identified. Three negative clones were also sequenced (clone 6, 9, and 10) and three additional Fab sequences were also identified (Fab-4, 5, and 6). Fab 1 and Fab 6 contained internal "TAG" amber stop codons, which lead to no Fab expression in HB2151 host cells. Therefore, only four Fabs (Fabs 2, 3, 4 and 5) were subjected to soluble expression and soluble ELISA.

TABLE 5

Summary of DNA Sequencing

| Fabs | Clones | Positions of Internal "TAG" stop codons | |
|---|---|---|---|
| 1 | 1 | In VL and VH | Positive clones |
| 2 | 3 | No | |
| 3 | 7 | No | |
| 4 | 6 | No | Negative clones |
| 5 | 9 | No | |
| 6 | 10 | In VL | |

Other Embodiments

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in art are intended to be within the scope of the invention.

All publications, patent applications, and patents mentioned in this specification are herein incorporated by reference to the same extent as if each independent publication was specifically and individually incorporated by reference.

What is claimed is:

1. An antibody or functional derivative thereof comprising a light chain variable domain and a heavy chain variable domain, wherein the light chain variable domain comprises a complementarity determining region (CDRL1) comprising the sequence of GASQSVSSSYLA (SEQ ID NO:11), a CDRL2 comprising the sequence of ASSRATGIPD (SEQ ID NO:12), and a CDRL3 comprising the sequence of YGSSPPVT (SEQ ID NO:13); and wherein the heavy chain variable domain comprises a CDRH1 comprising the sequence of SYDIN (SEQ ID NO:14), a CDRH2 comprising the sequence of WMNPNSGNTGYAQKFQG (SEQ ID NO:15), and a CDRH3 comprising the sequence of GKGSGYYNY (SEQ ID NO:16).

2. The antibody or functional derivative thereof of claim 1, wherein the light chain variable domain of said antibody or functional derivative thereof, comprises the sequence of SEQ ID NO:4 and the heavy chain variable domain comprises the sequence of SEQ ID NO:6.

3. The antibody or functional derivative thereof of claim 1, wherein said functional derivative of the antibody is selected from a single chain antibody (scFv), a Fv, a Fab, a Fab', or a F(ab')₂.

4. The antibody or functional derivative thereof of claim 3, wherein said functional derivative of the antibody does not contain an Fc domain.

5. An antibody or functional derivative thereof comprising a light chain variable domain and a heavy chain variable domain, wherein the light chain variable domain comprises a CDRL1 comprising the sequence of TGTSSDVGGYNYVS (SEQ ID NO:17), a CDRL2 comprising the sequence of DVSNRPSGVSN (SEQ ID NO:18), and a CDRL3 comprising the sequence of YAGSSTLV (SEQ ID NO:19); and wherein heavy chain variable domain comprises a CDRH1 comprising the sequence of SYDIN (SEQ ID NO:14), a CDRH2 comprising the sequence of WMNPNSGNTGYAQKFQG (SEQ ID NO:15), and a CDRH3 comprising the sequence of GRGFDWLKNFDY (SEQ ID NO:20).

6. The antibody or functional derivative thereof of claim 5, wherein the light chain variable domain of said antibody or functional derivative thereof, comprises the sequence of SEQ ID NO:8 and the heavy chain variable domain comprises the sequence of SEQ ID NO:10.

7. The antibody or functional derivative thereof of claim 5, wherein said functional derivative of the antibody is selected from a single chain antibody (scFv), a Fv, a Fab, a Fab', or a F(ab')₂.

8. The antibody or functional derivative thereof of claim 7, wherein said functional derivative of the antibody does not contain an Fc domain.

9. A pharmaceutical composition comprising an antibody or functional derivative thereof of claim 1 and a pharmaceutically acceptable excipient.

10. A pharmaceutical composition comprising an antibody or functional derivative thereof of claim 5 and a pharmaceutically acceptable excipient.

11. A kit comprising an antibody or functional derivative thereof of claim 1 and a therapeutic antibody.

12. A kit comprising an antibody or functional derivative thereof of claim 5 and a therapeutic antibody.

13. A method for treating a proliferative disease in a patient in need thereof, said method comprising administering to said patient the antibody or functional derivative thereof of claim 1 and a therapeutic antibody, wherein said antibody or functional derivative thereof and said therapeutic antibody are administered simultaneously, or within 14 days of each other, in amounts that together are sufficient to treat said proliferative disease.

14. The method of claim 13, wherein said therapeutic antibody is selected from the group consisting of rituximab, MT201, 17-1A, herceptin, alemtuzumab, lym-1, bevacizumab, cetuximab, and IL-2 receptor alpha-directed monoclonal antibodies.

15. The method of claim 14, wherein said antibody or functional derivative thereof and said therapeutic antibody are administered simultaneously.

16. The method of claim 15, wherein said antibody or functional derivative thereof is formulated together with said therapeutic antibody.

17. The method of claim 13, wherein said proliferative disease is characterized by neoplastic cells expressing CD59.

18. A method for treating a disease caused by a pathogen expressing a CD59- or CD59-like molecule in a patient in need thereof, said method comprising administering to said patient the antibody or functional derivative thereof of claim 1.

19. The method of claim 18, further comprising administering a therapeutic antibody against said pathogen, wherein said antibody or functional derivative thereof and said therapeutic antibody are administered simultaneously, or within 14 days of each other, in amounts that together are sufficient to treat said pathogenic disease.

20. The method of claim 18, further comprising administering an antibody specific for a virus selected from the group consisting of human cytomegalovirus (HCMV), human T-cell leukemia virus type 1, HIV-1, simian immunodeficiency virus, Ebola virus, Herpesvirus saimiri virus, influenza virus, and vaccinia virus.

21. The method of claim 19, wherein said therapeutic antibody is specific for a microbial parasite selected from the group consisting of *Naegleria fowleri* and *Schistosoma manosni*.

22. The method of claim 19, wherein said antibody or functional derivative thereof and said therapeutic antibody are administered simultaneously.

23. The method of claim 22, wherein said antibody or functional derivative thereof is formulated together with said therapeutic antibody.

24. A method for treating a proliferative disease in a patient in need thereof, said method comprising administering to said patient the antibody or functional derivative thereof of claim 5 and a therapeutic antibody, wherein said antibody or functional derivative thereof and said therapeutic antibody are administered simultaneously, or within 14 days of each other, in amounts that together are sufficient to treat said proliferative disease.

25. The method of claim 24, wherein said therapeutic antibody is selected from the group consisting of rituximab, MT201, 17-1A, herceptin, alemtuzumab, lym-1, bevacizumab, cetuximab, and IL-2 receptor alpha-directed monoclonal antibodies.

26. The method of claim 25, wherein said antibody or functional derivative thereof and said therapeutic antibody are administered simultaneously.

27. The method of claim 26, wherein said antibody or functional derivative thereof is formulated together with said therapeutic antibody.

28. The method of claim 24, wherein said proliferative disease is characterized by neoplastic cells expressing CD59.

29. A method for treating a disease caused by a pathogen expressing a CD59- or CD59-like molecule in a patient in need thereof, said method comprising administering to said patient the antibody or functional derivative thereof of claim 5.

30. The method of claim 29, further comprising administering a therapeutic antibody against said pathogen, wherein said antibody or functional derivative thereof and said therapeutic antibody are administered simultaneously, or within 14 days of each other, in amounts that together are sufficient to treat said pathogenic disease.

31. The method of claim 29, further comprising administering an antibody specific for a virus selected from the group consisting of human cytomegalovirus (HCMV), human T-cell leukemia virus type 1, HIV-1, simian immunodeficiency virus, Ebola virus, Herpesvirus saimiri virus, influenza virus, and vaccinia virus.

32. The method of claim 30, wherein said therapeutic antibody is specific for a microbial parasite selected from the group consisting of *Naegleria fowleri* and *Schistosoma manosni*.

33. The method of claim 30, wherein said antibody or functional derivative thereof and said therapeutic antibody are administered simultaneously.

34. The method of claim 33, wherein said antibody or functional derivative thereof is formulated together with said therapeutic antibody.

* * * * *